United States Patent
Tsai et al.

(10) Patent No.: US 7,598,653 B2
(45) Date of Patent: Oct. 6, 2009

(54) SURFACE ACOUSTIC WAVE BIO-CHIP

(75) Inventors: Yi-Chin Tsai, Taipei County (TW);
Wen-Pin Hsieh, Miaoli County (TW);
Kai-Cheng Chang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 187 days.

(21) Appl. No.: 11/622,469

(22) Filed: Jan. 12, 2007

(65) Prior Publication Data
US 2007/0159027 A1    Jul. 12, 2007

Related U.S. Application Data

(60) Provisional application No. 60/759,170, filed on Jan. 12, 2006.

(30) Foreign Application Priority Data

Jul. 7, 2006    (TW) .............................. 95124777 A

(51) Int. Cl.
*H01L 41/08* (2006.01)
(52) U.S. Cl. .................................. 310/313 R
(58) Field of Classification Search ............. 310/313 R, 310/313 D
See application file for complete search history.

(56) References Cited

U.S. PATENT DOCUMENTS

| | | | |
|---|---|---|---|
| 3,978,731 A * | 9/1976 | Reeder et al. ................. | 73/703 |
| 4,598,224 A | 7/1986 | Ballato | |
| 5,306,644 A | 4/1994 | Myerholtz et al. | |
| 5,571,944 A * | 11/1996 | Pfeifer et al. ............... | 73/24.04 |
| 5,992,215 A | 11/1999 | Caron et al. | |
| 6,321,588 B1 | 11/2001 | Bowers et al. | |
| 6,621,192 B2 * | 9/2003 | Lu et al. .................. | 310/313 A |
| 6,710,515 B2 | 3/2004 | Lu et al. | |
| 6,803,698 B2 * | 10/2004 | Tabota .................... | 310/313 R |
| 7,027,921 B2 * | 4/2006 | Kalantar-Zadeh et al. ...... | 702/2 |
| 7,205,701 B2 * | 4/2007 | Liu et al. ................. | 310/313 R |
| 2004/0072208 A1 | 4/2004 | Warthoe et al. | |

OTHER PUBLICATIONS

Gi-Beum Kim et al. "Development of Biosensor Using Surface Acoustic Wave." The 30th Annual Conference of the IEEE Electronics Society, Nov. 2-6, 2004, Busan, Korea; pp. 1546-1549.
J.F. Vetelino et al. "Theory, Design and Operation of Surface Generated Acoustic Wave Sensor." 1994 IEEE MTT-S Digest pp. 505-508.
Ryszard M. Lec et al. "Acoustic Wave Biosensor." Proceedings of the 20th Annual International Conference of the IEEE Engineering in Medicine and Biology Socity, vol. 20, No. 6, 1998. pp. 2779-2784.

* cited by examiner

*Primary Examiner*—Mark Budd
(74) *Attorney, Agent, or Firm*—Jianq Chyun IP Office

(57) ABSTRACT

A surface acoustic wave (SAW) bio-chip is designed with signal processing circuits. The chip can achieve precise measurements or detection quantitatively via the difference between the experiment-control mode, and followed by amplification and filtering of the signal processing circuits. By changing the designs of the substrate, quantitative detection toward different analyses can be achievable.

16 Claims, 4 Drawing Sheets

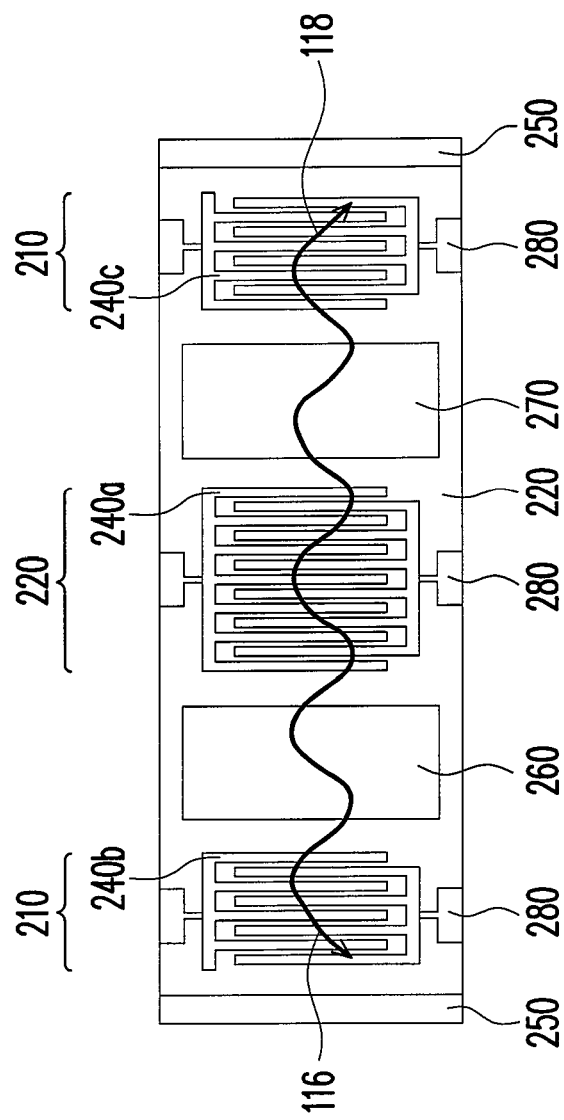
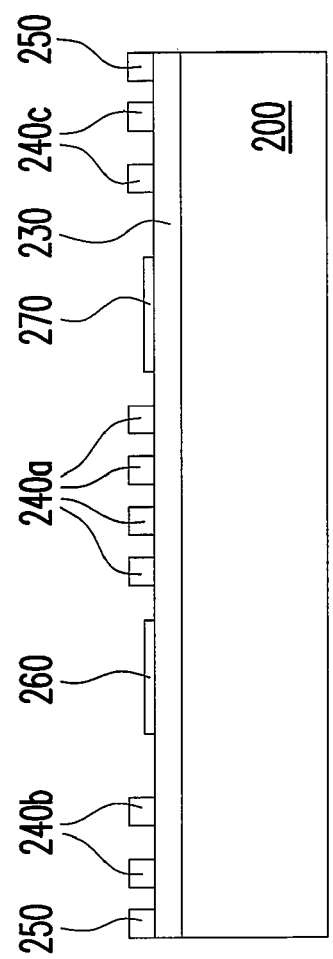
FIG. 2A
FIG. 2B

SURFACE ACOUSTIC WAVE BIO-CHIP

CROSS-REFERENCE TO RELATED APPLICATION

This application claims the priority benefit of U.S.A. provisional application Ser. No. 60/759,170, filed on Jan. 12, 2006, all disclosures are incorporated therewith. This application also claims the priority of Taiwan application serial no. 95124777, filed Jul. 07, 2006. All disclosure of the Taiwan application is incorporated herein by reference.

BACKGROUND OF THE INVENTION

1. Field of Invention

The present invention is related to a technology of bio-chip, and more particular to a bio-chip using the surface acoustic wave (SAW) mechanism, capable of detecting a bio sample.

2. Description of Related Art

The surface acoustic wave (SAW) technology has been used in wide application. According to its design mechanism, it can be used to detect various changes in physical or chemical properties, and can be used to design a detector for detecting, for example, temperature, pressure, twist, or even the volatile of gas or chemical material.

Certainly, the SAW apparatus can also be used in bio-chemical or biomedical detection. Due to the design with high sensitivity and simple structure, the SAW apparatus has been well considered in applications. Generally, the SAW apparatus needs to be covered with a bio-recognition coating layer for detecting the bio sample, such as a specific bio-chemical or biomedical material.

In the bio-chemical or bio-medical field, several type of biomarkers have been known to help the estimation or diagnosis of various diseases or the relating symptoms. As a result, the prevention or precaution on developing or worsening of diseases can be made. For example, the status of cardiovascular diseases can be estimated or diagnosed by using markers of CK-MB (CK, Myoglobin) and Troponin-I/T. If the Troponin-I/T is the sample to be detected, generally, since the concentration of Troponin-I/T in blood is very low, it therefore needs to be detected by a sensor with high sensibility. However, in the conventional technology, the detecting sensibility for the Troponin-I/T is relatively low. This conventional technology for detecting the Troponin-I/T still has disadvantages to be further solved.

Reviewing the prior art, U.S. Pat. Nos. 6,321,588; 5,306,644; and 5,992,215 have disclosed relating detection tools in combination with SAW for signal amplification. The signal is then detected by circuit. These prior arts are concentrating on analyzing the chemical material and gas molecules. Although the U.S. Pat. No. 4,598,224 also discloses a relating technology but the quantity analysis and noise treatment are not considered. The publications or published patents are generally on the application of communication and high frequency device but not on the application of bio-sensor. In addition, some of them may be used to detect the micro change in physical quantity, such as analysis of existence of gas or chemical material in small quantity.

In addition, the conventional SAW apparatus can use, for example, the Inter-Digital Transducer (IDT) design. The publication of "The 30$^{th}$ Annual Conference of the IEEE Electronics Society, Nov. 2-6, 2004, Busan, Korea; pp 1546-1549" by Gi-Beum Kim et al. has also introduced the SAW sensor. The SAW sensor includes the IDT's on a piezoelectric substrate. The IDT's are formed from thin metal film. When an electric signal with appropriate frequency is applied to the input IDT, SAW is launched on the surface of the substrate due to the reverse piezoelectric effect. The SAW propagates across the surface of the substrate and is converted back into an electric signal by the output IDT. The operating frequency f, is determined by the IDT finger spacing $\omega_s$, finger width $\omega_f$, wavelength $\lambda$, and SAW velocity $v_s$ according to the relation of $f=v_s/\lambda$ where $\lambda=2(\omega_s+\omega_f)$. The SAW velocity However, if a mass load is disposed on the path of the SAW, the SAW velocity $v_s \propto \sqrt{c/\rho}$ is proportional to the elasticity and density of the substrate and the associated mass load on it. Therefore, the mass load can be detected. The detail can be referred to Gi-Beum Kim et al. and can be understood by the person with ordinary skill. The further detail is omitted here.

However, due to the improper implementing structure of IDT in the SAW apparatus, the performance is not good and could be affected by the noise and echo phenomenon, and then the discerning capability and sensitivity get low. Since the quantity analysis in micro-amount is strongly needed in the current trend, it is strongly desired to have high precision with the least amount of sample.

The conventional design of IDT sensor has many disadvantages, such as easily producing noise. Since the IDT is very sensitivity, the surface is easily affected resulting in several issues. For example, the IDT cannot be integrated into an integrated circuit and it is not easy to handle on property under batch production. As a result, the development is quite limited. In these reasons, some experts in this field change the concerning point and develop the applications of SAW technology on the electronic filter. This technology has been developed for about half century. The efforts from experts on developing this technology are not much in recent years. However, based on the IDT mechanism, the bio-chip with better performance is still needed in continuous development.

SUMMARY OF THE INVENTION

Generally, the present invention uses the SAW device to have further applications on, for example, biomedical and bio-chemical detection, and pharmacology application such as the selection of target medicine.

The present invention uses a SAW bio-chip, having a SAW device with a sensing region and a signal processing circuit on a substrate.

In the present invention, a SAW bio-chip, which can amplify the signal different and filter the noise.

In the present invention, a testing sample region and a referencing sample region are provided under the same background conditions in measurement. By input from single acoustic signal generator, the testing sample region and the referencing sample region are arranged in symmetrical implementation, such as left-right symmetry. By detecting the difference between two signals from the testing sample region and the referencing sample region, the discerning precision with respect to the reference sample can be improved.

In the present invention, an absorption region can be located at the corresponding periphery of the SAW device. Under proper design and selection on material and size of the absorption region, the echo can be effectively absorbed or cancelled.

The present invention provides a SAW bio-chip, including a substrate having a property of piezoelectric material. An insulating layer is implemented on the substrate. A SAW generating region is implemented on the insulating layer, wherein a first SAW signal and a second SAW signal, being substantially identical, are generated by interaction with the substrate and travel on the insulating layer. A first SAW transduction region is implemented on the insulating layer to receive the first SAW signal for producing a first electric signal. A second SAW transduction region is implemented on the insulating layer to receive the second SAW signal for producing a second electric signal. When the bio-chip is in operation, a reference sample and a testing sample are disposed on the insulating layer and respectively on the routes of the first SAW signal and the second SAW signal. The two routes are symmetric with respect to the SAW generating region.

The present invention also provides SAW bio-chip, including a substrate having a property of piezoelectric material. An insulating layer is implemented on the substrate. A first Inter-Digital Transducer (IDT) unit is implemented on the insulating layer, wherein a first SAW signal and a second SAW signal, being substantially identical, are generated by interaction with the substrate and travel on the insulating layer. A second IDT unit is implemented on the insulating layer to receive the first SAW signal for producing a first electric signal. A third IDT unit is implemented on the insulating layer to receive the second SAW signal for producing a second electric signal. When the bio-chip is in operation, a reference sample and a testing sample are disposed on the insulating layer and respectively on the routes of the first SAW signal and the second SAW signal. The two routes are symmetric with respect to the SAW generating region.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 2A-2B are top view and cross-section view, schematically illustrating a structure of SAW bio-chip, according to an embodiment of the present invention.

DESCRIPTION OF THE PREFERRED EMBODIMENTS

The present invention proposes a SAW bio-chip, capable of improving quantity precision in detecting a bio sample, in which the noise and the echo signal can at least be reduced. The present invention further uses a reference sample for producing a reference signal, so as to measure the signal difference of the measuring signal from the testing sample. As a result, under the same operation condition, the error in conventional method, caused by the separating measurements with different background conditions, can be reduced. Further, the noise and the residual echo of the acoustic signals can be further reduced by a filter and an acoustic absorbing structure. The precision can be further improved. In addition, since the measured quantity is the difference between the testing sample and the reference sample, the difference can be quantified, so as to determine the probability about whether or not the testing sample is the same as the reference sample. Some embodiments are provided for descriptions but the present invention is not just limited to the embodiments.

Figure 1:
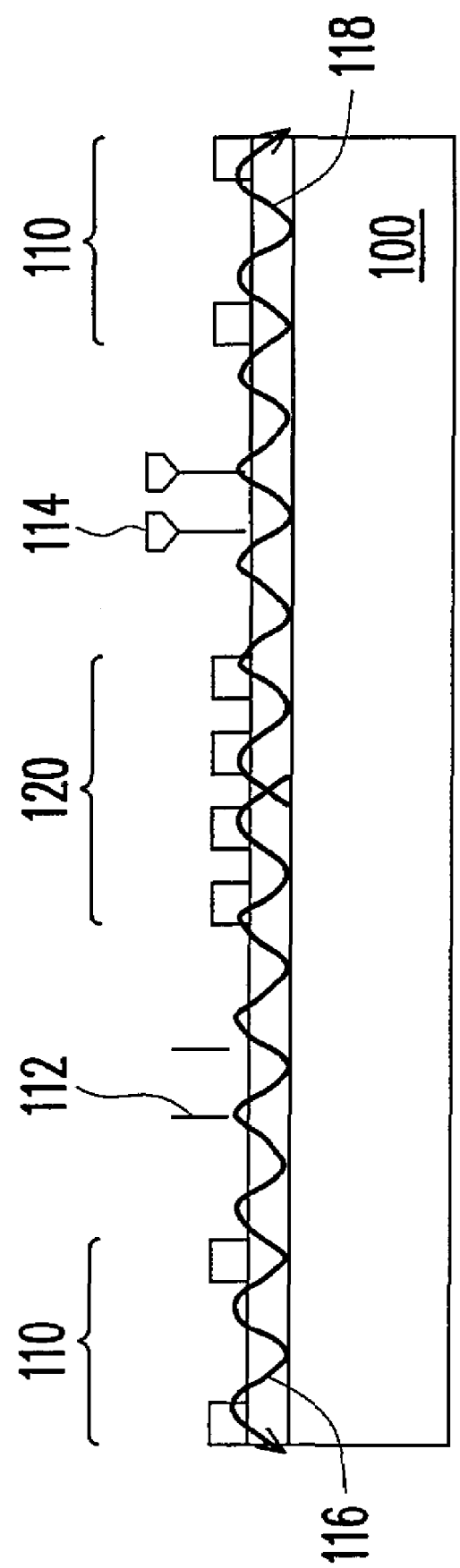
FIG. 1 is a cross-sectional view, schematically illustrating a structure of SAW bio-chip, according to an embodiment of the present invention.

FIG. 1 is a cross-sectional view, schematically illustrating a structure of SAW bio-chip, according to an embodiment of the present invention. In FIG. 1, a substrate 100 is divided into a middle region 120 and two side regions 110 at a symmetrical arrangement with respect to the middle region 120. The substrate 100 includes the property of piezoelectric material. For example, the substrate 100 is a block layer of piezoelectric material, or a structural block layer having a piezoelectric layer disposed on a bottom layer. The middle region 120 can be implemented with a SAW generating structure, such as an IDT structure, capable of converting an alternative electric signal into surface acoustic wave based on the piezoelectric property of the substrate 100. For example, the surface acoustic waves are generated and travel in two opposite directions as shown by the wavy arrows. An insulating layer is implemented between the substrate 100 and the IDT unit, for isolation and serving as a wave guide layer. As a result, the physical wave generated from the middle region 120 can propagate out. This physical wave in the present invention is called surface acoustic waves 116 and 118. The two side regions 110 are also implemented with the IDT units for respectively receiving the two surface acoustic waves 116 and 118 in two directions. In order to have better comparison effect, the middle regions is distant to the two side regions 110 in equal distance, and the IDT units at the two side regions 110 are identical, so as to again convert the received SAW signals into the electric signals for analysis. In other words, the two side regions 110 corresponding to the single middle region 120 have the symmetrical routes, preferably a symmetrical disposition in left-to-right symmetry. Certainly, the two side regions with respect to the middle region 120 may have an including angle. However, the two routes for the two side regions 120 to the middle region 120 are still in symmetric arrangement.

In operation, for example, a position at the left side of the middle region 120 can be disposed with a reference sample 112, such as a bio reference sample. At the same time, a corresponding position at the right side of the middle region 120 can be disposed a bio testing sample 112, such as a bio sample to be detected. Further, for example, the foregoing positions of the bio reference sample 112 and the bio testing sample 114 can be exchanged. The changes, when the SAW passes the bio testing sample and the bio reference samples, can be simultaneously measured by the IDT units at the two side region 110. Since the operation condition are the same, the measured signals from the IDT unit at the two side regions 110 can be, for example, analyzed in difference. This can at least reduce the error caused in conventional method by separating measurement under different operation conditions. The structure of SAW bio-chip is to be described in further detail as follows.

FIG. 2A and FIG. 2B are top view and cross-section view, schematically illustrating a structure of SAW bio-chip, according to an embodiment of the present invention. In FIG. 2A and FIG. 2B, an insulating layer 230 is formed on a substrate 200, and also serves as a wave guide layer, called SAW propagation layer. The substrate 200, as previously described, is a substrate having the property of piezoelectric material. In FIG. 2A and FIG. 2B, a piezoelectric layer is taken as the example for description. The middle region 220 of the insulating layer 230 is formed with SAW generating structure 240a. Via the medium of the insulating layer 230, a first surface physical wave 116 and a second surface physical wave 118 being substantially identical are generated, and preferably propagating in two opposite directions. The SAW generating structure 240a is, for example, a pair of metal bar layers, that is, IDT unit. The two terminals 280 of the SAW generating structure 240a can be applied an alternative electric signal to the IDT unit. The alternative electric signal can be, for example, a period wave such as semi-period wave, sine wave, square wave, triangle wave. The generated electric field would generate the stress on the piezoelectric material, so as to produce the SAW. Further, according to the geometric shape of the metal bar layer, such as the length, width, bending gap, and size with the piezoelectric property of material, a specific propagation mode of the SAW can be generated.

Further, another two identical SAW transduction structure 240b and 240c are implemented on the insulating layer at the two side regions 210, so as to receive the two SAW signals and convert them into two electric signals, which are output at the terminal 280. In addition, after the SAW signals pass the SAW transduction structure 240b and 240c at two side regions 210, it may have residual SAW signals in continuous propagation. In this situation, for example, an acoustic absorbing structure 250 can be additionally implemented, so as to avoid the improper reflection (or called echo) from the SAW signals in the insulating layer, causing measurement error.

When the bio-chip is in operation, the reference sample can be disposed on one of the two routes of the SAW signals, such as the position of the reference sample region 260, by a contact layer. In addition, the testing sample can be disposed on another one of the routes of the SAW signals, such as the position of the testing sample region 270. It preferably has the same distance for the position of the reference sample region 260 and the position of the testing sample region 270 in corresponding to the position of the SAW generating structure 240a. As a result, when the reference sample is compared with the testing sample in measuring difference, most of system error can be removed due to the operation condition being substantially the same.

It can be noted that the reference sample and the testing sample are disposed on the insulating layer 230. Further, the SAW generating structure 240a is used to generate the SAW signals while the SAW transduction structures 240b and 240c are used to receive the measuring SAW signals. Here, the SAW generating structure 240a and the SAW transduction structures 240b, 240c can be, for example, designed by the IDT structure. However, the other mechanism with similar function can be use, too. The present invention is not limited to the IDT design.

In addition, generally, the three regions 210, 220 are preferably arranged in a straight line and symmetry. However, this is not the only way in arrangement. It can be modified into other arrangements while the reference sample and the testing sample can be measured under the operation condition. For example, the three regions 210, 220 are not necessary to be in straight line. Further, according to the design by implementing the IDT unit at the region 220, if the SAW signal is generated in isotropic direction, such as the structure in circular shape, then several side regions 210 with respect to the middle region 220 can be set, and several testing samples can be measured at the same time. The present invention proposes the comparison between the testing sample and the reference sample, such as the analysis on difference, so as to quantify the measured results. Under this principle, various designs can be made and it is not necessary to restrict to a specific design.

Figure 3:
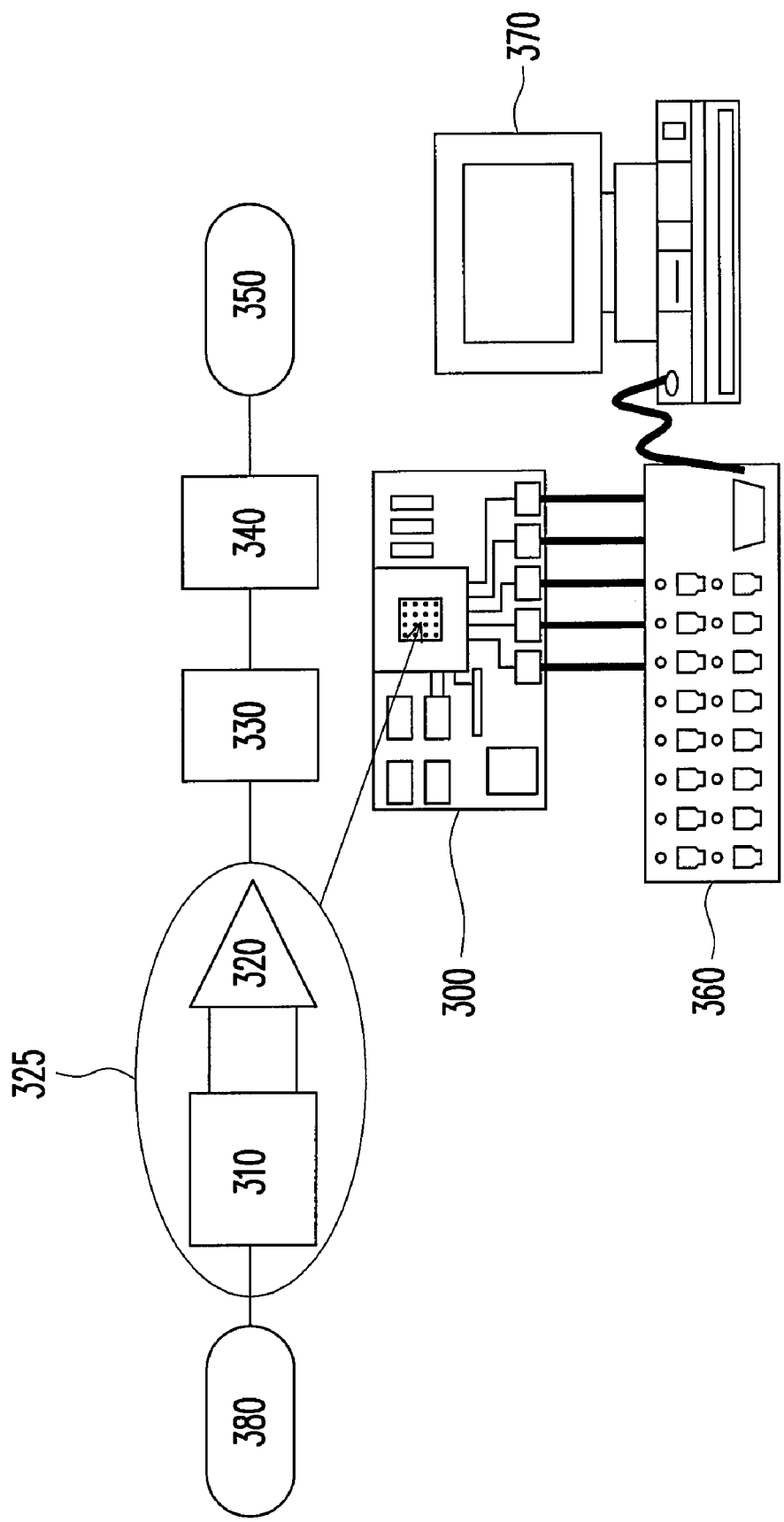
FIG. 3 is a circuit diagram, schematically illustrating the circuit structure of the SAW bio chip, according to another embodiment of the present invention.

Continuously, the signals measured by the SAW transduction structures 240b, 240c can be further processed and analyzed. FIG. 3 is a circuit diagram, schematically illustrating the circuit structure of the SAW bio chip, according to another embodiment of the present invention. In FIG. 3, the signals measured from SAW transduction structures 240b, 240c can be, for example, processed and analyzed by using external circuit in association with computer system. However, in order to have convenient use in bio-chip, a portion of circuit can be formed on a substrate 300.

In FIG. 3, in addition to the structure as described in FIGS. 2A-2B, a portion of circuit structure can be also formed on the substrate 300. In other words, the implementation of the circuit structure allows the bio-chip itself already carries a signal processing circuit, so as to have convenient use. However, the circuit structure is not absolutely necessary to be formed on the substrate 300. In other words, the bio-chip can, for example, output the electric signals to the external circuit unit for processing. In the following example for descriptions, a portion of the circuit is formed on the substrate 300. For example, a conducting wire structure 380 and the SAW sensor 310 lead the output signals from the SAW transduction structures 240b, 240c at the side region 210 to a differential amplifier 320. The SAW sensor 310 and the differential amplifier 320 can be integrated into a circuit unit 325. The differential amplifier 320 can take out the signal difference between the testing sample and the reference sample and properly amplifies the difference. Alternatively, the differential amplifier 320 can be a subtracting device for subtracting the two input signals. After the differential amplifier 320, according to the actual need, the signal is further input to a signal processing unit 330 and a filter 340. The signal processing unit 330 can further adjust the signal or even digitized the signal, and so on. The filter 340 can filter the noise. In other words, some signal processing circuits can be pre-formed on the substrate 300. The signal can be output at the terminal 350 for the analysis by the external computer system 370. The computer system 370 may need to process several bio-chips at the same time, wherein an interface of multiplexer 360 can be used to select the one to be analyzed. However, the foregoing analysis is just the example for the subsequent analyzing and processing, the process flow is not necessary to be the same as the embodiment.

In addition, form the fabrication point of view, for example, the semiconductor fabrication process can be used, including deposition, photolithography, etching, and so on. Further for example, the IDT unit at the regions 210, 220 can be patterned at the same time, so as to obtain the desired structure. The detail can be understood by the one in ordinary skill and is not further described.

Figure 4A:
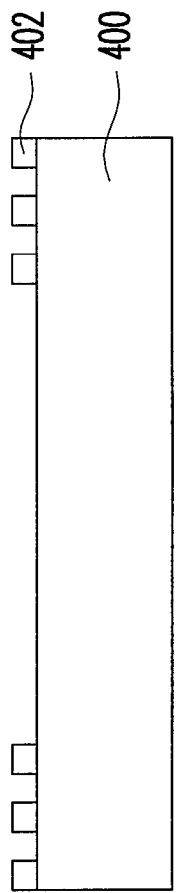
FIGS. 4A-4C are cross-sectional views, schematically illustrating a fabrication process for a SAW bio-chip, according to an embodiment of the present invention.
Figure 4B:
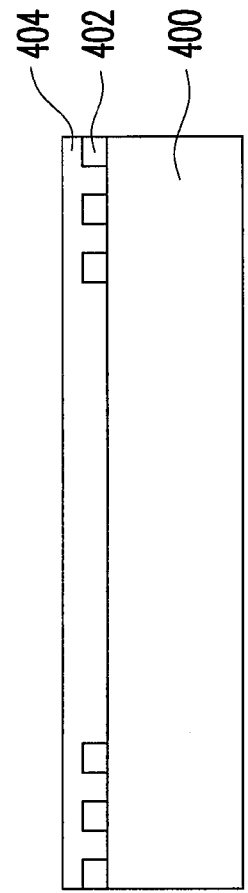
Figure 4C:
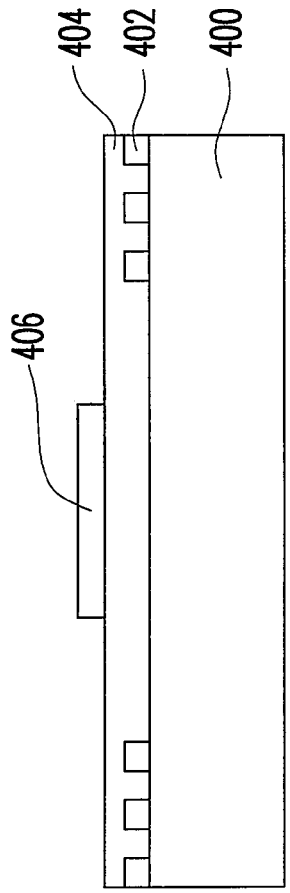

In the following descriptions, an example for fabricating the FIGS. 4A-4C are cross-sectional views, schematically illustrating a fabrication process for a SAW bio-chip, according to an embodiment of the present invention. In FIG. 4A, substrate 400, such as ST-Cut Quartz with the piezoelectric property, is provided. A metal layer, such as gold layer, is formed and patterned by photolithographic and etching processes on the substrate, so as to form the IDT 402. Here, the direction of the crystal lattice needs in consideration. In FIG. 4B, an insulating layer such as silicon oxide layer is deposited over the substrate 400. The insulating layer is, for example, 1 micron in thickness. In FIG. 4C, another metal layer, such as gold layer, is formed and patterned by photolithographic and etching process to form the metal layer 406 on the insulating layer 404 to serve as a contact layer for adapting the sample.

Remarkably, the elements of surface Love wave usually have advantages of low attenuation and high sensitivity. However, the surface Love Wave is not always generated by any kind of layered structure. In order to generate the surface Love wave for the need of SAW, it needs the wave guiding layer on the substrate. The usual material for the wave guide layer can be silicon oxide, zinc oxide, or PMMA, in which silicon oxide is preferred because of low wave loss and resistance in alkalinity and acidity. In other words, the insulating layer 404 also servers as the wave guiding layer for the SAW.

The SAW bio-chip of the present invention has the analysis in high quality and quantity. The acoustic wave is converted in to AC output by the IDT. The IDT, the insulating layer and the structures at the regions of testing sample and reference sample can be formed by film deposition. The testing sample can be chemical product, food, agricultural product, or bio sample. The physiology analytes or bio sample can be blood, plasma, saliva, cerebral spinal fluid, lymph, urine, immunoglobulins, the immunoglobins complementary analytes, viruses, therapeutic drugs, hormones, proteins, steroids, neurotransmitters, receptors, glycosylated proteins, carbonhydrates, neucleic acids, cells, cancer markers, neucleotides, or heptens.

When the AC signal is input, the input terminal is connected to the periodic wave in fix frequency. The selection of the periodic wave can be adjusted according to the substrate, the insulating layer, and the IDT in a distance and width. The periodic wave with fix frequency can be semi-period wave, sine wave, square wave, triangle wave and so on. The alternating electric field can be generated between the electrodes. The piezoelectric crystal in responding to the electric filed produces deformation, so that the electric energy is converted into acoustic energy. Further, the signal passes the testing sample and the reference sample and the signals frequency is changed due the mass effect. Then, the signal processing circuit output the changes acoustic signal and convert the acoustic signal into the electric signals, which are further amplified and filtered in noise, and then output for the external measurement.

According to the preferred embodiment of the present invention, the signal difference between the testing sample and the reference sample is collected, so as to obtain the result. In the present invention, the noise and the echo between phase and phase can be significantly reduced by the design at the absorption region in material and size, and a symmetric design for the sample region (testing sample region and reference sample region) of the bio-chip. In addition, since the film deposition is used to form the sample regions, the amount of the samples in detection can be reduced. Since the only small amount of the sample is needed, the precision and the subsequent management and analysis on signal can be simplified and more quantified, so as to improve the competition on chip performance.

The present invention employs the proper symmetry design for the absorption region, the IDT with selected material and size under test and specific design, and the symmetric design for the testing sample region and reference sample region. Further, the structure formed by the fabrication process allows the simultaneous measurements for the testing sample region and reference sample region. As a result, the key factors of insufficient analyses in quantity and quality for the conventional method can be overcome by the present invention. The insulating layer can be formed by film deposition process. The signal processing circuit and the absorption region surrounding at the symmetric periphery of the SAW bio-chip can together reduce the noise and echo. The quantity analysis can be done by the differential circuit to discern the signal difference, and the signal can be amplified by signal processing circuit. In order for adapt various physiology analytes, they can be adapted by simply changing the materials at the sample regions.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A surface acoustic wave (SAW) bio-chip, comprising:
a substrate, having property of piezoelectric material;
an insulating layer, implemented on the substrate;
a SAW generating region, implemented on the insulating layer, wherein a first SAW signal and a second SAW signal, being substantially identical, are generated from a same SAW element by interaction with the substrate and travel on the insulating layer;
a first SAW transduction region, implemented on the insulating layer to receive the first SAW signal for producing a first electric signal;
a second SAW transduction region, implemented on the insulating layer to receive the second SAW signal for producing a second electric signal; and
a circuit unit, implemented on the substrate to receive the first electric signal and the second electric signal for processing the signals,
wherein when the bio-chip is in operation, a reference sample is disposed over the insulating layer and at one of two routes of the first SAW signal and the second SAW signal, a testing sample is disposed over the insulating layer and at another one of the two routes of the first SAW signal and the second SAW signal,
wherein the two routes are symmetric with respect to the SAW generating region.

2. The SAW bio-chip of claim 1, wherein the SAW bio-chip outputs the first electric signal and the second electric signal to an external circuit unit for processing the signals.

3. The SAW bio-chip of claim 1, further comprising a plurality of acoustic absorbing structures for respectively absorbing a residual signal from the first SAW signal and the second SAW signal.

4. The SAW bio-chip of claim 1, wherein the two routes are symmetric in left to right.

5. The SAW bio-chip of claim 1, the insulating layer also serves as an acoustic wave guide layer.

6. The SAW bio-chip of claim 1, wherein the testing samples includes one selected from the group consisting of blood, plasma, saliva, cerebral spinal fluid, lymph, urine, immunoglobulins, the immunoglobins complementary analytes, viruses, therapeutic drugs, hormones, proteins, steroids, neurotransmitters, receptors, glycosylated proteins, carbonhydrates, neucleic acids, cells, cancer markers, neucleotides, heptens.

7. The SAW bio-chip of claim 1, wherein the SAW generating region is input with an alternating signal comprising semi-period wave, sine wave, square wave, triangle wave.

8. The SAW bio-chip of claim 1, wherein the reference sample and the testing sample are disposed on the insulating layer by a contact layer.

9. The SAW bio-chip of claim 1, wherein the substrate is a block of piezoelectric material.

10. The SAW bio-chip of claim 1, wherein the substrate comprises a bottom layer and a piezoelectric material layer on the bottom layer.

11. A surface acoustic wave (SAW) bio-chip, comprising:
a substrate;
an insulating layer, implemented on the substrate;
a first intr-digital transducer (IDT) unit, implemented on the insulating layer, wherein a first SAW signal and a second SAW signal, being substantially identical, are generated from the first IDT unit by interaction with the substrate and travel on the insulating layer;

a second IDT unit, implemented on the insulating layer to receive the first SAW signal for producing a first electric signal;

a third IDT unit, implemented on the insulating layer to receive the second SAW signal for producing a second electric signal; and a circuit unit, implemented on the substrate, to receive the first electric signal and the second electric signal for processing the signals, wherein when the bio-chip is in operation, a reference sample is disposed over the insulating layer and at one of two routes of the first SAW signal and the second SAW signal, a testing sample is disposed over the insulating layer and at another one of the two routes of the first SAW signal and the second SAW signal, wherein the two routes are symmetric with respect to the first IDT unit.

12. The SAW bio-chip of claim 11, wherein each of the IDT units comprises a pair of metal bar layers.

13. The SAW bio-chip of claim 11, wherein the SAW bio-chip outputs the first electric signal and the second electric signal to an external circuit unit for processing the signals.

14. The SAW bio-chip of claim 11, further comprising a plurality of acoustic absorbing structures for respectively absorbing a residual signal from the first SAW signal and the second SAW signal.

15. The SAW bio-chip of claim 11, wherein the two routes are symmetric in left to right.

16. The SAW bio-chip of claim 11, the insulating layer also serves as an acoustic wave guide layer.

* * * * *